(12) United States Patent
Nautiyal

(10) Patent No.: US 6,495,362 B1
(45) Date of Patent: *Dec. 17, 2002

(54) BIOLOGICALLY PURE CULTURE OF BACTERIA WHICH SUPPRESSES DISEASES CAUSED BY PATHOGENS IN CHICKPEA CROPS AND A CULTURE OF BACTERIA COMPRISING A STRAIN OF PSEUDOMONAS FLUORESCENS

(75) Inventor: Chandra Shekhar Nautiyal, Lucknow (IN)

(73) Assignee: Council of Scientific & Industrial Research, New Delhi (IN)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/889,916

(22) Filed: Jul. 10, 1997

(30) Foreign Application Priority Data

Sep. 3, 1996 (IN) ...................................... 1952/Del/1996

(51) Int. Cl.⁷ ............................ C12N 1/20; A01N 63/00
(52) U.S. Cl. ................ 435/252.34; 435/876; 424/93.47
(58) Field of Search .................... 424/93.47; 435/253.3, 435/876, 252.34

(56) References Cited

U.S. PATENT DOCUMENTS 5,256,544 A * 10/1993 Rogers et al. ................ 435/42
5,260,302 A * 11/1993 Fattori et al. ................. 435/34

OTHER PUBLICATIONS

Vidhyasekaran et al., "Development of formulation of *Pseudomonas fluorescens* for control of chickpea wilt", Plant Disease, Aug. 1995, vol. 79, No. 8, pp. 782–786.*
Myatt et al., "Potential for biological control of Phytophthora root rot of chickpea by antagonistic root–associated bacteria", Australian Journal of Agricultural Research, 1992, vol. 44, No. 4, pp. 773–784.*
Kaiser et al., "Biological control of seed rot and preemergence damping–off of chickpea with fluorescent pseudomonads", Soil Biol. Biochem., 1989, vol. 21, No. 2, p. 2690273.*
Weller et al., "Population dynamics of *Pseudomonas fluorescens* Q29z–80 onchickpea crops", In: improving plant prodctivity with rhizosphere bacteria, Proceedings of the third internatonal workshop on plant growth–promoting rhiobacteria,Adelaide, Australi.*
Scher et al., "Amethod for assising the root–colonozing capacity of bacteria onmaize", Can. J. Microbiol., 1984, vol. 30, pp. 151–157.*
Compeau et al., "Survival of rifampin–resistant mutants of *Pseudomonas fluorescens* and *Pseudomonas putida* in soil systems", Appled and Environmental Microbiology, Oct. 1988, pp. 2432–2438.*
A Method for Selection and Characterization of Rhizosphere–Competent Bacteria of Chickpea, Current Microbiology 34, pp. 12–17, Jan. 1997.
Selection of Chick–Pea–Rhizosphere–Competent *Psedudomonas fluorescens* NBRI 1303 Antagonist to *Fusarium oxysporum* f.sp. Cicieri, *Rhizoctonia bataticola* and *Pythium sp.* Current Microbiology 35 (1977) pp. 52–58, Jul. 1997.

* cited by examiner

Primary Examiner—Irene Marx
Assistant Examiner—Vera Afremova
(74) Attorney, Agent, or Firm—Lowe Hauptman Gilman & Berner, LLP

(57) ABSTRACT

A simple sand-live soil assay method for large scale screening of the rhizosphere-competent bacteria, effective in suppressing plant pathogens has been developed. Screening for chickpea rhizosphere competitive bacteria having biological control property was conducted at three different stages: development of screening method for large scale initial selection of bacteria isolates from chickpea rhizosphere, testing of biocontrol activity under in vitro conditions and screening of antibiotic resistant mutants for rhizosphere competence in nonsterile field soil, which assay is used to disclose one *Pseudomonas fluorescens* NBRI 1303 (ATCC 55939) which is effective in suppressing plant pathogens, including *Fusarium oxysporum f. sp. ciceri, Rhizoctonia bataticola* and Phthium sp. in chickpeas and the purified bacterial strain can be used as active agent for biocontrol compositions and can also be used for enhancement of chickpea plant growth and yield, as well as for the production of antibiotics directed towards phytopathogenic fungal diseases.

14 Claims, 2 Drawing Sheets

BIOLOGICALLY PURE CULTURE OF BACTERIA WHICH SUPPRESSES DISEASES CAUSED BY PATHOGENS IN CHICKPEA CROPS AND A CULTURE OF BACTERIA COMPRISING A STRAIN OF *PSEUDOMONAS FLUORESCENS*

FIELD OF THE INVENTION

This invention relates to a novel bacteria strain of *Pseudomonas fluorescens* designated as ATCC 55939 and a method for large scale screening of native rhizosphere microflora, to identify and characterize naturally occurring rhizosphere-competent biocontrol bacteria from non-sterilized soil, which could effectively colonize plant roots. The present invention relates more specifically to the use of a novel strain of Pseudomonas fluorescens as a biocontrol agent for controlling plant fungal disease particularly those diseases caused by fungus of the genus Fusarium sp., Rhizoctonia sp. and Pythium sp.

BACKGROUND OF THE INVENTION

The fungal pathogens play a major role in the development of diseases on many important field and horiculture crops which often results in the poor plant yields. Considering the cost of chemical pesticides and hazard involved, biological control of plant diseases is now increasingly capturing the imagination of plant microbiologists. Frequent failure of the added microorganisms to become established is not surprising because the biological associations and antagonisms within the ecosystem determine the composition of the microflora, the climax population being a reflection of the physical and chemical characteristics of the habitat.

A major factor in the unsuccessful commercialization of rhizosphere bacteria has been the inconsistency of field test results. Reasons for the reported variability include nonpersistence on seed before it is planted and poor bacterial establishment on seed and roots, please refer Burr, T, J., and A. Caesar, Crit. Rev. Plant Sci. 2: 1–20 (1984); Gaskins, M. H. et al. Ecosystems Environ. 12: 99–116 (1985); Liang, L. et al. Appl. Environ. Microbiol. 44: 708–714 (1982); O'Sullivan, D. J., and F. O'Gara, Micrbiol. Rev. 56: 662–676 (1992); Schrotk, M. N., and J. G. Hancock. Disease suppressive soil and root colonizing bacteria. Science 216: 1376–1381 (1981); Weller, D. M., Ann. Rev. Plant Pathol. 26: 379–407 (1988). The introduced microorganism must colonize plant roots and demonstrate rhizosphere competence before its further utilization as biological control and/or, plant growth promoting agent. When the proper bacterial strain is used, plant roots are extensively colonized by the introduced strain, which suggests a close bacteria-plant association that allows for beneficial plant growth or disease protection, see for example, Schmidt, E. L., Ann. Rev. Microbiol. 33: 355–376 (1979).

The isolation and development of plant beneficial bacteria applicable to a varietv of crops. soils. and locations will depend on the development of improved detection and screening procedures that more rapidly identify beneficial bacteria. While prior methods have been somewhat effective, such methods have had inherent shortcomings. For example, the current methods which are required to ascertain bacterial root colonization capacity are laborious and often produce highly variable results. Bennett and Lynch J. Gen. Microbiol. 125: 95–102 (1981), developed a closed test tube assay for measuring root colonization capacity of bacteria under gnotobiotic conditions which proved useful for studying specific microbial interactions in the rhizosphere. However, it is not possible to extrapolate results obtained in sterilized soils to those expected under field conditions, see for example, Klopper, J. W. Plant growth-promoting rhizobacteria and plant growth under gnotibiotic conditions. Phytopathology. 71: 642–644 (1981). Scher, F. M. et al. Can. J. Microbiol. 30: 151–157 (1984) measured the root colonization capacity of bacteria on maize in raw soil-sand closed test tube assay and demonstrated that root population densities determined in the soil-sand assay were comparable with those determined with plants grown in soils under greenhouse conditions. However, Scher et al. did not compare the competitive fitness of Rif mutants with the wild type strain. Compeau, G. et al. Appl. Environ. Microbiol. 54: 2432–2438 (1988) have demonstrated that colonization of soil by a species which is isogenic to a challenging organism may preempt the colonization of the soil by the second organism. This is true even when organisms display identical fitness. This interaction may be important in the failure of introduced strains to increase in number when introduced into their own environment. Thus, it is desirable to obtain novel strains of biocontrol agents which effectively control the growth of plant pathogens, particularly fungi, and are able to aggressively compete with indigenous bacteria and other microflora that exist in the rhizosphere of the plant.

SUMMARY OF THE INVENTION

This invention relates to a simple sand-live soil assay method, for large scale screening of the rhizosphere-competent bacteria that are effective in suppressing plant pathogens, that has been developed. Screening for chickpea rhizosphere competitive bacteria having biological control property was conducted at three different stages: development of screening method for large scale initial selection of bacteria isolates from chickpea rhizosphere, testing of biocontrol activity under in vitro conditions and screening of antibiotic resistant mutants for rhizosphere competence in nonsterile field soil, which assay has disclosed one *Pseudomonas fluorenscens* NBRI 1303 (ATCC 55939) that is effective in suppressing plant pathogens, including *Fusarium oxysporum f. sp. ciceri, Rhizoctonia bataticola* and Pythium sp. in chickpeas. The purified bacterial strain can be used as an active agent for biocontrol compositions and can also be used for enhancement of chickpea plant growth and yield, as well as for the production of antibiotics directed against phytopathogenic fungal diseases.

Accordingly, it is an object of the present invention to provide a method of raw (non-sterile) soil assay for large scale screening of native rhizosphere microflora of chickpeas that identifies and characterizes naturally occurring rhizosphere bacteria that effectively colonize chickpea roots.

Another object of the present invention is to provide a biocontrol agent that is useful in methods for suppression of fungal infection in chickpeas and thereby enhances plant yields.

Still another object of the present invention is the use of a biological control agent(s) that produces one or more metabolites capable of inhibiting fungal pathogens of chickpeas or other plants. The use of such a biological control agent instead of seed treatment and soil treatment chemical fungicides allows reduction of environmental contamination.

Yet another object of the present invention is to provide a method for biocontrol of pathogenic fungi *F. oxysporum f. sp. ciceri, R. bataticola* and Pythium sp. in plants by application of an isolated *P. fluorenscens* strain.

Other objects and advantages of the invention will become apparent from the ensuing description.

Accordingly, the present invention provides a method for large scale screening of native rhizospheric competent bacteria for strains that will control plant pathogens thereby promoting plant growth in field grown chickpea crops, said method comprising:

a. harvesting chickpea crops from a disease-suppressive field after five months of plant growth;
b. subjecting the said harvested crop roots to drying in the field for a post harvest period of four weeks;
c. isolating bacterial strains from the said chickpea roots by standard methods;
d. selecting rifampin resistant bacterial strains showing growth comparable to wild type on agar plates containing 100 (µg rifampin/ml);
e. evaluating the root colonization capability of the bacterial strain obtained in step (d) in the greenhouse on the basis of average root colonization values of rifampin resistance strains after four weeks of post planting period;
f. selecting bacterial strains from the strains evaluated in step (e) with $10^7$–$10^8$ CFU/g root; and
g. screening a novel strain from the bacterial strains obtained in step (f) for its invitro inhibition against *F. oxysporum f. sp. ciceri, R. bataticola* and *Pythium sp.* to produce a biologically pure culture of bacteria that suppresses diseases caused by pathogens in chickpea crops as determined by passing the screen test of the invention.

Basically, the invention provides a biologically pure culture of the bacteria of the invention wherein said culture of bacteria comprises a strain of *Pseudomonas fluorenscens*. The culture of bacteria comprises a strain of *Pseudomonas fluorescens* that has been deposited at ATCC and designated as ATCC 55939.

The invention also relates to a screening method wherein initial screening time is reduced in the present assay system by directly inoculating the rifampin resistant strains into seeds without checking for the stability of the mutation. The present invention also provides a screening method in which initial screening time is reduced as compared to the current assay system by directly inoculating the rifampin resistant strains into seeds without any taxonomic identification.

Another aspect of the invention is to provide a method wherein the novel bacterial strain isolated in the step (g) is used in greenhouse seed bacterization, providing 10 to 25% or more increase in germination of chickpea seedlings in the presence of phytopathogenic fungal disease conducive soil from the trial fields.

Yet another embodiment of the invention is to provide a method wherein the novel strain isolated in the step (g) is used in greenhouse seed bacterization, providing 35 to 60% increase in survival rate of chickpea seedlings in the presence of the phytopathogenic fungal disease conducive soil from the trial fields.

Further, the invention provides a method wherein the novel strain isolated in step (g) is used in greenhouse seed bacterization to provide more that 10 to 25% increase in dry weight of chickpea seedlings exposed to phytopathogenic fungal disease conducive soil from the trial fields. The novel strain isolated in step (g) is used in greenhouse seed bacterization to provide more than 15 to 25% increase in the length of chickpea shoots growing in the presence of phytopathogenic fungal disease conducive soil from the trial fields. The applicants also noticed that the novel strain isolated in step (g) provided 10–15% increase in shoot length in chickpea plants in fields naturally infested with *F. oxysporum f. sp. ciceri, R. bataticola* and Pythium sp. In addition, the present novel strain of bacteria isolated in step (g) provided 15–20% increase in shoot dry weight in chickpea plants in fields that were naturally infested with *F. oxysporum f. sp. ciceri, R. bataticola* and Pythium sp.

The invention further provides a method in which the novel strain of bacterium isolated in step (g) provided 20 to 30% increase in seed dry weight in chickpea plants in fields that were naturally infested with *F. oxysporum f. sp. ciceri, R. bataticola* and Pythium sp. The present strain isolated in step (g) was used in greenhouse seed bacterization providing 15 to 25% increase in the length of chickpea roots in the presence of phytopathogenic fungal disease conducive soil from the trial fields.

Still another aspect of the invention is to provide a method wherein the novel strain isolated in step (g) provides rhizospheric competence for the full growing season of the chickpea plant. The applicants also observed that the novel bacteria strain isolated in step (g) exhibits the capability to solubilize phosphate in the presence of salt (NaCl) in a concentration range of 0 to 5% and has the capability to solubilize phosphate at a temperature in the range 30–45° C. Further, it was observed that the present novel bacteria strain isolated in step (g) exhibits the capability of solubilizing phosphate at a pH in the range of 7–9.

The present invention relates to an improved method that requires less screening time for isolating and identifying naturally occurring rhizosphere-competent bacteria from non-sterilized soil. More specifically, the present invention relates to a novel *P. fluorescens* strain that can be used as a biocontrol agent for suppression of the pathogenic fungi *F. oxysporum f. sp. ciceri, R. bataticola* and Pythium sp. in chickpeas.

Current available methods require a lot of time to screen the native microorganisms for rhizospheric competence. In the present study, the screening time, compared to previous reports (see for example, Compeau, G. et al Appl. Environ. Microbiol. 54: 2432–2438 (1988); Juhnke, M. E. et al Appl Environ. Microbiol. 53: 2793–2799 (1987); Lewis, D. M. et al. an. J. Microbiol. 33: 343–345 (1987); Liang, L. et al Appl. Environ. Microbiol. 44: 708–714 (1982); Loper, J. E. et al Appl. Environ. Microbiol. 49: 416–422 (1985); Scher, F. M. et al. Can. J. Microbiol. 30: 151–157 (1984) Turco, R. F. et al. Soil Biol. Biochem. 18: 259–262 (1986)), has been reduced in two respects. First, Rif strains in the present assay system were directly inoculated into seeds without any check for the stability of the mutation. This stability check usually requires at least 25 passes through non-selective media. It is anticipated that any Rif strain that shows high CFU/g root 30 days after inoculation should by able to do so only if it is capable of sustained growth while competing against the native microorganisms. Secondly, no attempts have been made to taxonomically identify all the strains.

Using this method, one chickpea rhizosphere competent strain was selected after screening four hundred and seventy eight bacteria, and taxonomically identified as *Pseudomonas fluorenscens* NBRI 1303 which is also deposited in ATCC and designated as ATCC 55939.

The results indicate that *P. fluorescens* NBRI 1303 is an aggressive chickpea rhizosphere colonizer and can survive in the field at temperatures in the range of 0° C. to 55° C. In addition, this bacterial strain appeas to produce one or more antifungal metabolites which inhibit the growth of pathogenic fungi *F. oxysporum f. sp. ciceri, R, bataticola* and Pythium sp. or other fungal pathogens of chickpeas since the culture supernatant exhibits growth inhibitory effects for pathogenic fungi *F. oxysporum f. sp. ciceri, R. bataticola* and *Pythium sp.* Greenhouse test and field trial of *P. fluorescens* NBRI 1303 (ATCC 55939) demonstrated the usefulness of the strain as an inoculum for improved plant performance and therefore *P. fluorenscens* NBRI 1303 (ATCC 55939) may be used as a biocontrol agent.

The characteristics of the subject *P. fluorescens* NBRI 1303 (ATCC 55939) were determined according to the morphological and physiological descriptions provided in Bergy's Manual of Determinative Bacteriology. The taxonomic characteristics of the strain *Pseudomonas fluorescens* are given in Table 1.

TABLE 1

| Fluorescent pigment | + |
| --- | --- |
| Arginine dihydrolase | + |
| Oxidase reaction | + |
| Denitrification | − |
| Pyocyanine | − |
| Carotenoids | − |
| Hydrolysis of | |
| Gelatin | + |
| Starch | − |
| Carbon sources for growth | |
| Glucose | + |
| Sucrose | + |
| Sorbitol | − |
| Mannitol | + |
| Cellobiose | − |
| D-Galactose | + |
| 2-Ketogluconate | + |
| L-Arabinose | + |
| Propylene glycol | − |
| Ethanol | − |
| L-Ornithine | + |
| Glycine | − |
| DL-Tryptophan | − |
| D-Alanine | + |
| DL-Arginine | + |

A representative isolate of the present invention has been deposited with the American Type Culture Collection, 10801 University Boulevard, Manassas, Va., 20110-2209, USA in accordance with the Budapest Treaty. This isolate is *P. fluorescens* strain NBRI 1303 assigned number ATCC 5939 deposited Feb. 21, 1997.

In addition to the other properties noted above, the novel strain *P. fluorescens* NBRI 1303 (ATCC 55939) also has the following qualities which are important for use as a biological control agent for chickpeas:

(i) being a naturally occurring isolate that does not require any genetic manipulations, to be effective (ii) being easily cultured and developed for commercial purposes, (iii) exhibiting capability to be rhizosphere competent for the full growing season, (iv) being suppressive of one or more phytopathogenic fungi, (v) exhibiting capability to soluble phosphorus, (vi) enhancing the yield of the host plant, (vii) being environment friendly, unlike chemical fungicides and fertilizers.

While the present method is described for evaluating rhizospheric colonization potential of a diverse group of naturally occurring bacteria isolated from non-sterilized soil from the rhizosphere of chickpeas as a host plant, *P. fluorescens* (organisms involved in promoting plant growth, suppression of plant disease, phosphate solubilization and phytoremediation), it should be recognized that the plants of the present invention may be any genus and/or species of plant or any genus and/or species of plant associated bacteria or combination thereof that will assist the plant growth through association with the plant root. These indigenous bacteria would then be available for use as biological control agents or plant growth-promoting bacteria applied as seed inoculants directly, and/or after genetic engineering.

The biocontrol agent or the substances produced by the biocontrol agent of the present invention may be used in any manner known in the art, including coating seeds in the presence or absence of carrier or direct seedling or soil treatment. While certain detailed and preferred embodiments have been disclosed for biological control of *Fusarium oxysporum f. sp. ciceri, Rhizoctonia bataticola* and *Pythium sp.* in chickpeas, numerous variations, modifications and embodiments are possible, and accordingly; all such variations, modifications and embodiments are to be regarded as being within the spirit and scope of the present invention.

DESCRIPTION OF THE PREFERRED EMBODIMENTS

Test for Rhizosphere Competence

Figure 1:
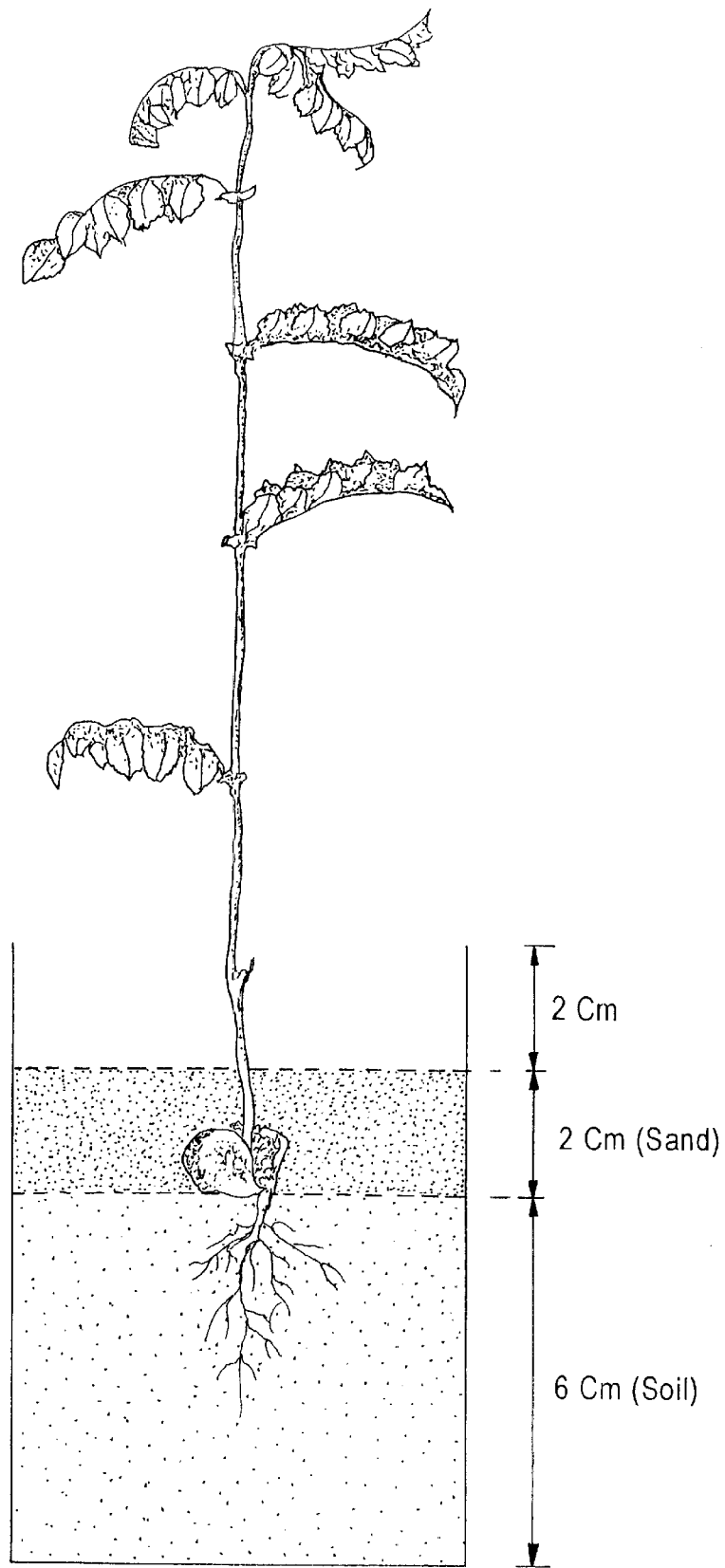
FIG. 1. depicts a sand-live soil assay system for screening rhizosphere competent bacteria wherein the assay was carried out in a 10 cm. vessel.

Various methods have been employed to test rhizosphere competence. The rhizosphere competence assay used in this invention is directed towards improving the time it takes to take measurements to screen the native microorganisms for rhizospheric competence by using a simple sand-live soil assay method for large scale screening of the rhizosphere-competent bacteria. In this greenhouse assay system, screening time was reduced in two ways. First, spontaneous chromosomal Rif strains were directly inoculated into seeds without any check for the stability of the mutation; and secondly, no attempts were made to taxonomically identify all the strains being screened for chickpea rhizosphere competence (Nautiyal, C.S. Curr. Microbiol. 34: 12–19 (1997).

Bacterial Strain Selection and Characterization

Bacterial strains were isolated from the roots of field-grown chickpea plants growing in a fungal diseases-suppressive field (free from the incidence of any fungal infection) in Lucknow, India. The chickpea crop was sown in the third week of October, 1994 and at that time the moisture content of the field soil was between 15–20%. Short spell of winter rains (10–12 mm) during December, 1994—January, 1995 was enough to keep the crop growing without any need of irrigation. To get a good grain yield of chickpeas, it is essential that chickpea fields are not watered beyond March. Maximum day time temperature at Lucknow in April, 1995 ranged from 38–45° C. This, followed by a one month spell of 46–50° C. in May 1995, in an unirrigated field, was enough to make the field soil very dry. These conditions are conducive to create water stress conditions for chickpea plant roots and their rhizosphere population. The chickpea crop was harvested, after plant growth of five months, in the fourth week of April, 1995. The rhizosphere bacterial population used in this work was isolated from the chickpea roots in May, 1995 four weeks after the harvest of five month old chickpea shoots. The common agronomic practice in India is to harvest the chickpea shoots about 5 cm from ground and then leave the roots in the field without any watering. This is done to increase the nitrogen (chickpeas being a legume crop) and carbon contents of the field soil, at the time of mulching in June. Thus, the chickpea roots were drying out during this period. There was no root decay. It is assumed that the bacteria that are present at this stage would be the most competitive rhizospheric bacteria that had colonized chickpea roots during initial root development and survived throughout the five month growing season of chickpea plants and one month postharvest high temperature and low water availability stress. However, the presence of the representatives of the secondary colonizer at this stage cannot be ruled out.

Roots were thoroughly washed with tap water for two minutes to remove all loosely adhering soil particles followed by washing with sterile 0.85% saline Milli Q water (MQW). The roots were then macerated in 0.85% saline MQW with a mortar and pestle. Serial dilutions of the homogenate were then plated on Nutrient agar (NA; Beef extract 5.0 gm, peptone 10.0 gm, sodium chloride 5.0 gm, agar 15 gm, distilled water 1000 ml, pH 7.2 or, beef extract 10.0 gm, peptone 5.0 gm, agar gm, distilled water 1000 ml, pH 7.0), pseudomonas growth agar (Tryptone 10.0 gm, protease peptone 10.0 gm, dipotassium phosphate 1.5 gm, magnesium sulphate 1.5 gm, agar 15 gm, distilled water 1000 ml, pH 7.2), Luria agar (LA; Tryptone 10.0 gm, yeast extract 5.0 gm, sodium chloride 5.0 gm, agar 15 gm, distilled water 1000 ml, pH 7.0), Tryptone-Yeast extract-Glucose agar (TYG; tryptone 10.0 gm, yeast extract 5.0 gm, glucose 10.0 gm, agar 15 gm, distilled water 1000 ml, pH 7.0), soil extract agar (glucose 2.0 gm, $K_2HPO_4$ 1.0 gm, soil extract 100 ml [1000 gm of soil is mixed with ml of distilled water and steamed in autoclave for 20 min and filtered through double filter paper], distilled water 900 ml, pH 7.0), as described earlier (Nautiyal, C. S. Curr. Microbiol. 33: 1–6 (1996). Bacteria representative of different morphological types present on the plates were selected and purified on minimal media based on AT salts (Nautiyal, C. S. et al. J. Bacteriol. 174: 2215–2221 (1992), which contained the following ingredients (per litre): glucose, 10.0 g; $KH_2PO_4$ 10.9 g; $(NH_4)_2SO_4$, $MgSO_4.7H_2O$, 0.16 g; $FeSO_4. 7H_2O$, 0.005 g; $CaCl_2.2H_2O$, 0.011 g; and $MnCl_2.4H_2O$, 0.002 g. The pH of the solution was adjusted to 7.0 by adding KOH. The microflora associated with the rhizosphere of roots of field-grown chickpea plants grown in a fungal diseases-suppressive field was identified as described earlier (Nautiyal, C. C., and P. Dion, Appl. Environ. Microbiol. 56: 2576–2579 (1990). Selection of Rifampin Resistance).

Spontaneous bacterial Rif strains were isolated on TGY agar plates containing 100 µg rifampin (from Sigma Chemical Co., St. Louis, Mo.) per ml by plating 100 g of overnight grown culture per plate. Resistance to rifampin was used because it is mediated by a mutation in a subunit of RNA polymerase (Sippel, A. E., and G. R. Hartmann, Biochem. Biophys. Acta 157: 2118–219 (1968), that is unusual among soil bacteria. The chromosomal nature of the mutation affords greater stability than occurs with plasmid-borne markers and is also advantageous since the mutation is not transferable (Compeau, G. et al. Appl. Environ. Microbiol. 54: 2432–2438 (1988)). Spontaneous bacterial Rif strains showing growth, comparable to wild type, on agar plates containing 100 µg rifampin, were selected for further studies. Serial dilution plating of the Rif strains was done on agar plates containing 0, 5, 25, 50 and 100 µg rifampin/ml. No significant differences in the viable counts were observed in different plates. Thus agar plates containing 50 µg rifampin/ml, an amount sufficient to inhibit the growth of other bacteria in non-sterilized soil, were used to recover Rif strains from the rhizosphere.

Seed Bacterization

Bacterial inoculum for chickpea (Cicer arietinum L.) seeds was prepared by scraping 48 hours of grown culture from AT plates with 10 ml of 0.85% saline MQW. Chickpea seeds were surface sterilized by gently shaking (80 R.P.M. on a reciprocal shaker) at 28° C. with 70% ethanol (5 Min), 20% household bleach (10 Min), followed by three rinses in sterilized MQW. After surface sterilization, seeds were soaked in the bacterial suspension for 4 hours at 28° C. on a reciprocal shaker at 100 R.P.M. Control seeds (uninoculated) were soaked in 0.85% saline MQW that had been washed from uninoculated AT plates. Inoculum levels of seeds was determined by agitating 4 seeds from each treatment and plating them, after serial dilution, on AT agar plate containing 50 µg/ml. Mean colony forming units (CFU) per seed were determined by averaging the CFU/g values of three populations in three replicates per treatment after 48 hours incubation of the plates at 28°.

Seed for treatments, in which mixtures of two isolates were used, were inoculated by using the same total number of bacteria for the inoculum as was used for the single-isolate treatments. Thus, one-half the normal amount of each isolate in the mixture was used.

Recovery of the Rhizosphere Bacterial Population

Recovery of the rhizosphere bacterial population was done by serial dilution plating of the homogenate on TGY media, in the presence of 50 µg rifampin/ml, on 15th, 30th and 45th day. No naturally occurring Rif bacteria were seen when root homogenates of uninoculated controls were plated from sterile or non-sterilized soils. Macerated root segments were dried for 4 days in an oven at 80° C. before measuring the weight. Average CFU/g (dry weight) of roots was determined as previously described for seeds, except with four replications per treatment.

*Fusarium oxysporum f. sp. ciceri, Rhizoctonia bataticola* and *Pythium sp.* were isolated from soil and infected plant parts of field-grown chickpeas (Cicerarietinum Lcv.Radhey) grown in a plot conducive to development of *F. Oxysporum f. sp. ciceri, R. bataticola* and *Pythium sp.* This field has been used for the past sixty years at Chandra Shekhar Azad University of Agriculture and Technology, Kanput, India to test new varieties of chickpeas, developed by plant breeders for their resistance against *F. oxysporum f. sp. ciceri, R. batatiocola* and *Pythium sp.* before their release to farmers.

Method to Test Fungal Inhibition in Vivo

Bacterial strains were tested, as per the modified method of Howell and Stipanovic, for their ability to inhibit growth of *F. oxysporum f. sp. ciceri, R. bataticola* and Pythium sp. on nutrient agar plates by streaking one to four single bacterial colonies around the edge of a 90-mm diameter petri plate and incubating at 28° C. for two days. An ager plug inoculum of the fungi (5-mm square) was then transferred to the center of the plate individually from a source plate of *F. oxysporum f. sp. ciceri, R. bataticola* and Pythium sp. and maintained on PAD for 2 to 7 days. After incubation for 2 additional days for *R. bataticola* and Pythium sp. and 5–7 additional days for *F. oxysporum f. sp. ciceri* at 28° C., inhibition zones were readily observed in the case of bacterial strains having the biocontrol activity, as the fungal growth around the streak was inhibited. While in case of bacterial strains not having biocontrol activity, fungal growth around the streak was not inhibited and the fungi grew towards the edge of the plate.

Root Colonization Assay

Thermocol trays (35×35 cm.) with 16 (4×4) places per tray (each place was 7 cm. width, 10 cm. depth and 1 cm. apart from each other) were used to grow plants. Each place was filled up to 6 cm. with either live (non-sterilized) or sterilized (1 hour at 121° C. for three consecutive days) soil, and further covered with 2 cm. of sterilized sand. Tap water (25 ml.) was added to each seed planting hole before planting seeds to adjust the soil to 20% moisture. One bacterial-treated seeds was added per hole and covered with 2 cm. sterilized coarse sand (FIG. 1 shows a vertical section of one place out of 16 places in the tray).

Plants were grown in a greenhouse and were carefully removed, at the specified time, from the pots and all root segments more than 5 mm below seed remnants were excised. This was done to ensure that only the bacteria that colonized the roots and not the bacteria that remained on seed coats were assayed. Excised roots were washed thoroughly to remove all the sand particles and then macerated in 0.85% saline MQW with a mortar and pestle. Rhizosphere bacterial population was quantified by serial dilution plating of the homogenate on TGY media, in the presence or absence of 50 $\mu$g rifampin/ml to enumerate the Rif sub population. No naturally occurring Rif bacteria were seen when root homogenates of uninoculated controls were plated from sterilized or nonsterilized soils. Macerated root segments were dried for 4 days in an oven at 80° C. before measuring the weight.

Isolation of Phytopathogenic Fungal Strains

Phytopathogenic fungal strains of *F. oxysporum f. sp. ciceri, R. bataticola* and Pythium sp. were isolated from the soil and infected roots of field-grown chickpeas (C. arietinum L. cv. Radhey) grown in disease-conducive field collected from Kanpur. The fungal isolates were grown and maintained on Potato Dextrose Agar (PDA, from HI-MEDIA Laboratories Pvt. Ltd., Bombay).

Cultivation of Phytopathogenic Fungi

Cultivation of fungi for plant assay was accomplished using a 1000 ml-Erlenmeyer flask with 100 g corn and 400 g coarse sand by autoclaving and after autoclaving moisture was adjusted to 15% with sterile distilled water. The flask was incubated at 30° C. individually with one 10 mm diameter agar plug from a nutrient agar culture of *F. oxysporum f. sp. ciceri, R. bataticola* and Pythium sp. in dark for 4 weeks. After four weeks the mixture was air-dried and ground and sieved to obtain particles 0.5 mm in size. Each inoculum was intimately mixed with sterile soil at 0.15% inoculum per total weight of soil, to give a final mixture of 0.45% inoculum of *F. oxysporum f. sp. ciceri, R. bataticola* and Pythium sp. per total weight of soil.

Assay of Bacterial Biocontrol Activity in Greenhouse

The experiment to examine the biocontrol activity of *P. fluorescens* NBRI 1303 (ATCC 55939) in greenhouse was carried out in four different sets of 30 chickpea seedlings each with treated and non-reated seeds (control). The plants were grown in sterile soil containing a mixture of 0.45% inoculum of *F. oxysporum f. sp. ciceri, R. bataticola* and Pythium sp. per weight of soil. In each set, data of 45-day old seedlings were noted with respect to the number of healthy and diseased seedlings, stunting of shoot height, drooping of leaves, root discoloration), dry weight, shoot length and root length of seedlings.

Field trials of *P. fluorescens* NBRI 1303 (ATCC 55939)

Field trials were carried out at Agra and Jhansi, Uttar Pradesh, India on the Farms of Department of Agriculture, State Government of Uttar Pradesh. For seed treatment, the. *P. fluorescens* NBRI 1303 (ATCC 55939) was grown as 1 liter shake culture in 2 liter Erlenmyer flasks in nutrient broth at 30° C. for 48 h at 180 RPM. The cells were centrifuged at 10.000 RPM for 10 min in a GSA rotor in a Sorvall RC5C Plus (Dupont, U.S.A.) centrifuge. The culture was then frozen and kept at –4° C. up to one month. Seeds were immersed in freshly thawed bacterial culture suspended in water (treatment or treatment control) for 30 min. The trials were seeded in the third week of October, 1995 and harvested after five months of growth, in the fourth week of March, 1996. The trials were established on a portion of experimental plots consisting of 26 rows, on which fungal infection had previously occurred. Seeds were planted 10 cm apart in a single row of 12 feet. The distance between one row and another was one foot. All results were collected from the middle rows, excluding two adjacent rows as guard rows, for both treatment and treatment controls. Population of *P. fluorescens* NBRI 1303 (Rif derivative of ATCC 55939). (CFU/g roots) was determined at the time of harvesting.

Colonization Ability

The bacterium identified as *P. fluorescens* and has been designated as *P. fluorescens* NBRI 1303, was selected for further studies. Rift derivative of *P. fluorescens* NBRI 1303 (ATCC 55939) (*P. fluorescens* NBRI 1303R) shows growth, comparable to its wild type, on Pseudomonas isolation agar containing 100 $\mu$g rifampin, and has in vitro inhibition activity against *F. oxysporum f. sp. ciceri, R. bataticola* and Pythium sp., comparable to *P. fluorescens* NBRI 1303 (ATCC 55939).

Evaluation of Ecological Fitness

Figure 2:
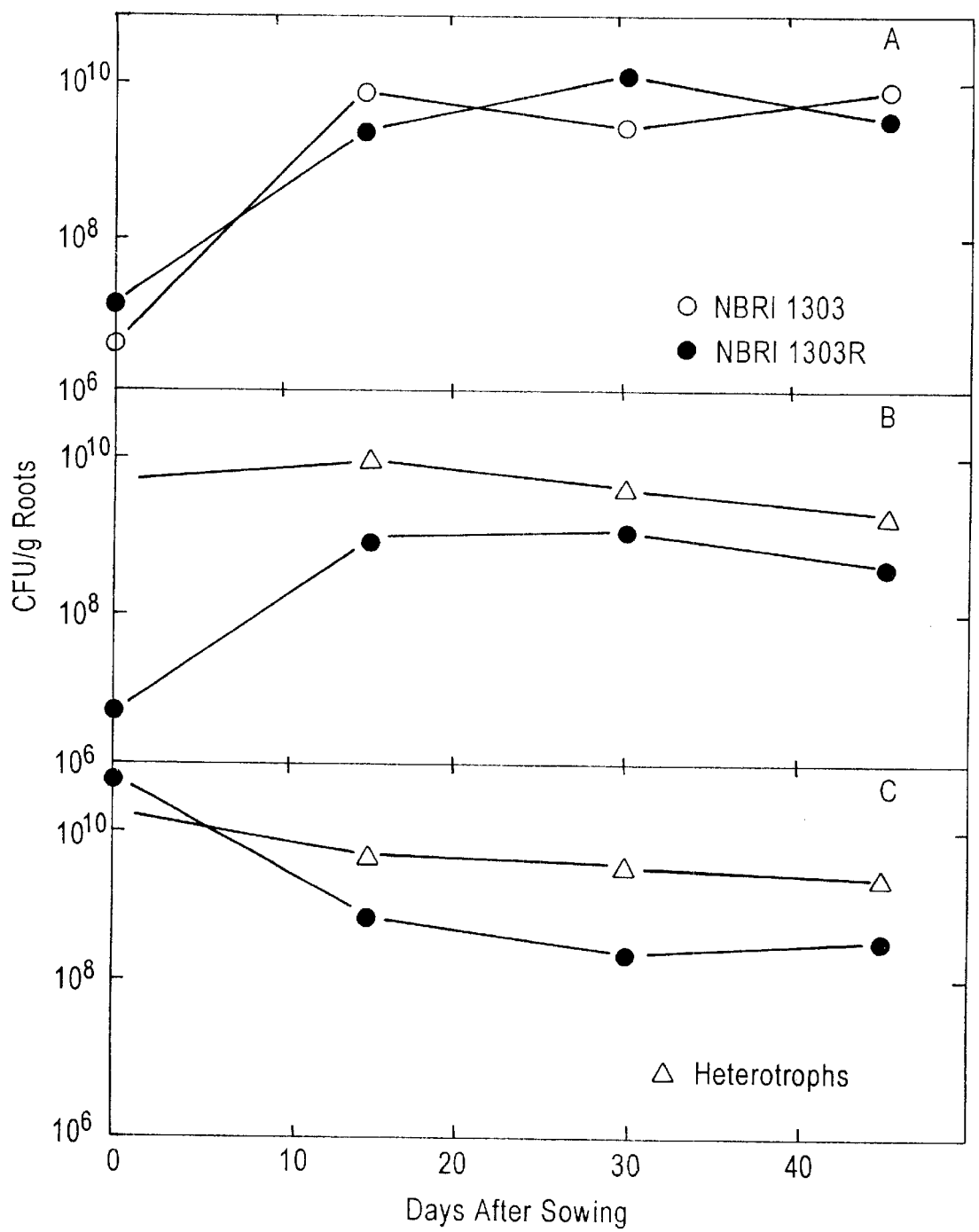
FIG. 2. depicts survival and competition of *Pseudomonas fluorescens* NBRI 1303 (ATCC 55939) and its Rif derivative *Pseudomonas fluorescens* NBRI 1303R (rifampin resistance derivative-Rif—Rif derivative of ATCC 55939) in the initial ratio (1:1) in the sterilized soil (A) in non-sterilized soil at a low concentration of NBRI 1303R ($5 \times 10^6$ CFU/seed) of seed bacterization (B) and high concentration ($5 \times 10^{10}$ CFU/seed) of NBRI 1303 of seed bacterization. (C) respectively. The hetrotropic population was counted on nutrient agar and *P. fluorescents* NBRI 1303R was identified by resistance to rifampin.

To evaluate the ecological fitness of the parent *P. fluorescens* NBRI 1303 (ATCC 55939) and its Rifr derivative *P. fluorescens* NBRI 1303R, both the strains were inoculated in the sterile soil, in the ratio of 1:1. *P. fluorescens* NBRI 1303R increased in titer at the same rate compared to its parent *P. fluorescens* NBRI 1303 (ATCC 55939) (FIG. 2A). This demonstrates that *P. fluorescens* NBRI 1303R (Rifr derivative *P. fluorescens* ATCC 55939) if equally competitive compared to that of its parent *P. fluorescens* NBRI 1303.

*P. fluorescens* NBRI 1303R was further studied in non-sterilized soil along with its parent *P. fluorescens* NBRI 1303. No gross changes were observed in the number and kinds of bacterial populations growing on nutrient agar plates during the course of the experiment (FIGS. 2B and 2C). Differences in the initial inoculum density amount of P. fluorescens NBRI 1303R did not influence the final population of P. fluorescens NBRI 1303R in the rhizosphere. The titer of P. fluorescens NBRI 1303R increased to about $1 \times 10^9$ CFU/g of root after 45 days in non-sterilized soil (FIGS. 2B and 2C). The continued presence of P. fluorescens NBRI 1303R for 45 days in non-sterilized soil showed that it has reached homeostasis after undergoing exchange with indigenous microflora and is not affected by the active and passive processes restricting soil community. This makes P. fluorescens NBRI 1303 ideally suited as a soil inoculant because of its potential for rapid and aggressive colonization. This population is greater than those previously reported for bacterial rhizosphere colonization by several workers. For example, Bennett, R. A. and J. M. Lynch, J. Gen. Microbiol. 125: 95–102 (1981) reported rhizosphete population averages of $5 \times 10_7$ cells/g of root. This feature is suggested as a disease control mechanism by preventing the invasion of detrimental soil microorganisms on to the root surface (Klopper, J. W. et al. Curr. Microbiol. 4: 317–320 (1980).

These studies confirmed the physiological and ecological fitness of P. fluorescens NBRI 1303R for its ability to compete in the rhizosphere of chickpeas in non-sterilized soil and biocontrol activity in greenhouse tests using fungal disease-conducive soil. The positive chickpea root-colonization ability of P. fluorescens and enhanced germination, survival and yield of chickpeas reported here confirm that fluorescent Pseudomonas sp. is indeed a potentially most promising group of plant growth-promoting rhizobacteria (PGPR) involved in the biocontrol of plant diseases [15, 23]. The 45% reduction of disease by seed bacterization makes P. fluorescens important in managing chickpea fungal disease-conducive soils.

Greenhouse Trial

Treatment with P. fluorescens NBRI 1303R of chickpea seeds placed in fungal disease-conducive soil resulted in increase of germination (25%), survival (45%), dry weight (17.2%) shoot length (17.8%) and root length (16.3%) compared to non-bacterized seeds (Table 2).

Table 2-Effect of seed bacterization in greenhouse by P. fluorescens NBRI 1303R on the germination, survival and growth of chickpea seedlings unsing phytopathogenis fungal disease-conducive soil from Kanpur

TABLE 2

| | Treatments[a] | | |
|---|---|---|---|
| Observations | Control | Treated | % increase over control |
| Germination (%)[b] | 70 | 95 | 25 |
| Survival (%)[c] | 40 | 85 | 45 |
| Dry weight (g)[d] | 0.29 | 0.35 | 17.2 |
| Shoot length (mm)[e] | 148 | 180 | 17.8 |
| Root length (mm)[f] | 113 | 135 | 16.3 |

[a]Non-bacterized (control) and bacterized (treated) seeds of chickpeas with P. fluorescens NBRI 1303R ($3 \times 10_6$ cells/seed).
[b]Values are the means of four replications of 30 seeds each.
[c]Values are the means of four replications of 30 seedlings each.
[d]Values are the mean dry weights (g) of 30 seedlings.
[e]Values are the mean shoot lengths (mm) of 30 seedlings.
[f]Values are the mean root lengths (mm) of 30 seedlings.

Field Trial

Field trial of P. fluorescens NBRI 1303R was conducted in Agra and Jhansi in fields naturally infested with F. oxysporum f. sp. ciceri, R. bataticola. Chickpea plants were harvested after five months. A general increase in the plant growth in both the field trials was detected similar to that obtained in the greenhouse test (Table 3).

Table 3. Rhizosphere colonization of chickpeas by P. fluorescens NBRI 1303R in field trials and effects on plant growth and yield.

TABLE 3

| | Treatments[a] | | |
|---|---|---|---|
| Field location, observations | Control | Treated | % increase over control |
| 1. Agra | | | |
| Shoot length (mm)[b] | 4014 | 4528 | 12.80 |
| Shoot dry weight (g)[c] | 1.35 | 1.60 | 18.51 |
| Seed dry weight (g/100 seeds)[d] | 17.85 | 21.41 | 19.94 |
| Rhizosphere colonization (CFU/g roots)[e] | 0.0 | $8.5 \times 10^5$ | N. A.[f] |
| 2. Jhansi | | | |
| Shoot length (mm) | 3850 | 4257 | 10.38 |
| Shoot dry weight (g) | 1.26 | 1.47 | 16.66 |
| Seed dry weight (g/100 seeds) | 19.30 | 24.18 | 25.28 |
| Rhizosphere colonization (CFU/g roots) | 0.0 | $4.8 \times 10^6$ | N. A. |

[a]Non-bacterized (control) and bacterized (treated) seeds of chickpeas with P. fluorescens NBRI 1303R ($5.7 \times 10_8$ CFU/seed).
[b]Values are the mean shoot lengths (mm) of four replications of 10 plants each.
[c]Values are the mean shoot dry weights (g) of four replications of 10 plants each.
[d].Values are the mean dry weights (g) of 100 seeds chosen at random from four replications of 10 plants each.
[e].Average P. fluorescens NBRI 1303R (CFU/g roots) populations were determined at the time of harvesting from four replications of three plants each.
[f].Not Applicable.

Compared to controls, treatment of chickpea seeds with P. fluorescens NBRI 1303R resulted in 19.94 and 25.28% increase in grain yield at Agra and Jhansi, respectively (Table 3). Colonization of P. fluorescens NBRI 1303R persisted throughout the growing season of five months and at the time of harvesting the population in two fields at Agra and Jhansi was $8.5 \times 10^5$ and $4.8 \times 10^6$ CFU/g roots, respectively. Recovery of P. fluorescens NBRI 1303R from field grown chickpea plant roots from $10^5$ to $10^6$ CFU/g roots and that it persisted on the roots of the chickpeas for the duration of the growing season is an indication of its aggressive colonization capacity and vigorous rhizosphere competitor potential.

Next only to nitrogen, phosphorus is the most important nutrient. Most of the essential plant nutrients, including phosphorus, remain in insoluble form in soil A large portion of inorganic phosphates applied to soil as fertilizer is rapidly immobilized soon after application and becomes unavailable to plants. Applying phosphate solubilizing microbes to soil as biofertilizer may alleviate this problem by solubilizing these immobilized products. Pseudomonas is an effective phosphate solubilizer and has improved root shoot biomass, straw and grain yield and phosphorus uptake in mung bean. Table 4 clearly indicates this fact.

TABLE 4

Phosphate solubilization by P. fluorescens NBRI 1303R

|  | 30° C. | 37° C. | 45° C. |
|---|---|---|---|
| pH 7.0 | | | |
| Salt conc. (%) | | | |
| 0.0 | 5 | 10 | 2 |
| 2.5 | 3 | 5 | 1 |
| 5.0 | 0 | 0 | 0 |
| pH 8.0 | | | |
| Salt conc. (%) | | | |
| 0.0 | 7 | 7 | 1 |
| 2.5 | 3 | 2 | 2 |
| 5.0 | 0 | 0 | 0 |
| pH 9.0 | | | |
| Salt conc. (%) | | | |
| 0.0 | 2 | 4 | 0 |
| 2.5 | 5 | 3 | 0 |
| 5.0 | 2 | 0 | 0 |

Phosphate solubilization was measured by the well established method of Pikoviskaya by measuring the clear hallow in mm on Pikovishaya agar plates containing insoluble tricalcium phosphate (r. Gupta R. singhal, A. Shankar, R. C. Kuhad and R. K. Saxena. (1994). A modified plate assay for screening phosphate solubilizing microorganisms is described in J. Gen. Appl. Microbiol. 40: 255–260).

DISCUSSION

Rhizosphere microorganisms affect growth and development of higher plants. If we are to understand the mechanisms and ultimately manipulate natural microbial communities in the rhizosphere, more studies on the dynamics of microbial populations in the rhizosphere of plants are needed. The competitive exclusion of deleterious rhizosphere organisms is directly linked to their ability to successfully colonize a root surface. In effect, all disease-suppressive mechanisms exhibited by bacteria are essentially of no real value unless these bacteria can successfully establish themselves in the root environment, for example see Gaffney, T. D. et al Molecular Plant-Microbe Interactions 7, 455–463 (1994) and Glandorf, D. C. M. et al. Appl. Environ. Microbiol. 60, 1726–1733 (1994). Since factors that influence root colonization are not known, it is difficult to design methods to predict this characteristic in vitro. Primary interest of this study was selection of wild-type rhizosphere competent bacteria having biological control activity against chickpea phytopathogens. Thus, a screening method was designed so that both rhizosphere competence and biological control potential could by evaluated. Screening for chickpea rhizosphere competitive bacteria having biological control property was conducted at three different stages: (I) development of screening method for large scale initial selection of bacteria isolates from chickpea rhizosphere, (ii) testing of biocontrol activity under in vitro conditions and (iii) screening of antibiotic resistant mutants for rhizosphere competence in nonsterile field soil.

The employment of beneficial bacteria to increase crop yields and to reduce the use of chemicals is an attractive development and the potential benefits may be considerable. Few methods have been developed for selecting bacterial strains for biological control. The present invention is the first detailed description of selecting rhizosphere-competent biocontrol bacterium that is antagonistic to three phytopathogenic fungi F. oxysporum f. sp. ciceri, R. bataticola and Pythium sp., of chickpeas. The results obtained from greenhouse test and field trials suggest the use of this aggressive chickpea root colonizing P. fluorescens NBRI 1303R (ATCC 55939) as a potentially useful biocontrol agent against F. oxysporum f. sp. ciceri, R. bataticola and Pythium sp. This invention demonstrates an increase in the efficiency of screening and detection of plant beneficial strains.

I claim:

1. A method of inhibiting infection of plants by F. oxysporum f. sp. ciceri, R. bataticola, and Pythium sp. which comprises contacting roots of said plant with the bacterium Pseudomonas fluorescens NBRI 1303 ATCC 55939 in an amount that is effective to inhibit infection of said plants.

2. A method of solubilizing an otherwise substantially insoluble phosphate which comprises contacting said substantially insoluble phosphate in the presence of a salt, other than a phosphate salt, with the bacterium Pseudomonas fluorescens NBRI 1303 ATCC 55939 in an amount that is effective to solubilize said phosphate.

3. A method of solubilizing phosphate as claimed in claim 2 wherein said contact is at a pH of about 7 to 9.

4. A method of solubilizing phosphate as claimed in claim 2 wherein said contact is in the presence of said salt in a concentration of up to about 5% by weight.

5. A method of solubilizing phosphate as claimed in claim 4 wherein said salt is NaCl.

6. A method of solubilizing phosphate as claimed in claim 2 wherein said contact is at a temperature of up to about 45° C.

7. A method of inhibiting infection of plants as claimed in claim 1 wherein said plant is chick pea.

8. A method of inhibiting infection of plants by the application of the bacterium Pseudomonas fluorescens NBRI 1303 ATCC 55939 in an amount that is effective to inhibit infection of said plants, as claimed in claim 7, further comprising recovering said bacterium Pseudomonas fluorescens NBRI 1303 ATCC 55939 from admixture with chick pea roots.

9. A method of improving the yield of chickpea plants growing in phytopathogenic fungal disease conducive soil as claimed in claim 7, further comprising inhibiting fungal infection of said plants by treating said plants with a bacterial strain from a culture of NBRI 1303 ATCC 55939 that is effective to enable an average of about 10 to 25% more chick pea seedlings to germinate than would have germinated after the same length of time in the absence of said effective amount of said bacterial strain.

10. A method of improving the yield of chick pea plants growing in phytopathogenic fungal disease conducive soil as claimed in claim 7 further comprising inhibiting fungal infection of said plants by treating said plants with a bacterial strain from a culture of NBRI 1303 ATCC 55939 in an amount that enables an average of about 35 to 60% more chick pea seedlings to survive than would have survived after the same length of time in the effective absence of said bacterial strain.

11. A method of improving the yield of chick pea plants growing in phytopathogenic fungal disease conducive soil as claimed in claim 1 further comprising inhibiting fungal infection of said plants by treating said plants with a bacterial strain from a culture of NBRI 1303 ATCC 55939 in an amount that enables chick pea seedlings to have an average dry weight of about 10 to 25% more than the dry weight of chick pea seedlings grown for the same length of time under the same conditions in the effective absence of said bacterial strain.

12. A method of improving the yield of chick pea plants growing in phytopathogenic fungal disease conducive soil as claimed in claim 1 further comprising inhibiting fungal infection of said plants by treating said plants with a bacterial strain from a culture of NBRI 1303 ATCC 55939 in an amount that enables an average seedling length of about 15 to 25% more than the average length of chick pea seedlings grown for the same length of time under the same conditions in the effective absence of said bacterial strain.

13. A method of improving the yield of chick pea plants growing in phytopathogenic fungal disease conducive soil as claimed in claim 1 further comprising inhibiting fungal infection of said plants by treating said plants with a bacterial strain from a culture of NBRI 1303 ATCC 55939 in an amount that enables growth of an average root length about 15 to 25% more than the average root length of chick pea plants grown for the same length of time under the same conditions in the effective absence of said bacterial strain.

14. A biologically pure culture of *Pseudomonas fluorescens* having all of the identifying characteristics of *Pseudomonas fluorescens* NBRI 1303 ATCC designation number 55939.

* * * * *